US011759760B2

(12) United States Patent
Bode et al.

(10) Patent No.: US 11,759,760 B2
(45) Date of Patent: Sep. 19, 2023

(54) APPARATUS AND PROCESS FOR THE AUTOMATED CHEMICAL SYNTHESIS OF COMPOUNDS

(71) Applicant: ETH Zurich, Zurich (CH)

(72) Inventors: Jeffrey William Bode, Zurich (CH); Benedikt Matthias Wanner, Zurich (CH); Kuang-Yen Chen, Zurich (CH); Vijaya Pattabiraman, Volketwswil (CH); Paula Louise Nichols, Schaffhausen (CH)

(73) Assignee: ETH Zurich, Zurich (CH)

( * ) Notice: Subject to any disclaimer, the term of this patent is extended or adjusted under 35 U.S.C. 154(b) by 505 days.

(21) Appl. No.: 16/065,940

(22) PCT Filed: Jan. 10, 2017

(86) PCT No.: PCT/EP2017/050400
§ 371 (c)(1),
(2) Date: Jun. 25, 2018

(87) PCT Pub. No.: WO2017/121724
PCT Pub. Date: Jul. 20, 2017

(65) Prior Publication Data
US 2019/0209995 A1    Jul. 11, 2019

(30) Foreign Application Priority Data
Jan. 12, 2016  (EP) .................................... 16150878

(51) Int. Cl.
*B01L 3/00*          (2006.01)
*B01J 19/00*         (2006.01)
(Continued)

(52) U.S. Cl.
CPC ............. *B01J 19/004* (2013.01); *B01J 14/00* (2013.01); *B01J 19/0013* (2013.01); *B01J 20/22* (2013.01);
(Continued)

(58) Field of Classification Search
CPC ................... B01J 2219/00585; B01J 19/0093
(Continued)

(56) References Cited

U.S. PATENT DOCUMENTS

| 6,500,609 B1 | 12/2002 | Ribeill et al. |
| 2002/0045265 A1* | 4/2002 | Bergh ..................... B01L 7/525 |
| | | 436/37 |

(Continued)

FOREIGN PATENT DOCUMENTS

GB          2520063 A        5/2015

OTHER PUBLICATIONS

Geogegan et al., "Bespoke SnAP Reagents for the Synthesis of C-Substituted Spirocyclic and Bicyclic Saturated N-Heterocycles", Organic. Letters, 2015, vol. 17, pp. 1934-1937.
(Continued)

*Primary Examiner* — Natalia Levkovich
(74) *Attorney, Agent, or Firm* — THE WEBB LAW FIRM (57) ABSTRACT

Provided is an apparatus for the automated synthesis of at least one chemical compound including: at least one cartridge including at least one first compartment for providing at least one first reagent for the chemical synthesis of the at least one compound; at least one second compartment for providing at least one second reagent for the chemical synthesis of the at least one compound, and at least one third compartment for purifying the at least one synthesized compound; at least one reaction container for providing the compounds to be fed into at least one of the compartments
(Continued)

of the cartridge and/or collecting the reaction product from at least one of the compartments of the cartridge; at least one solvent container at least two flow path selecting valves and at least one pump.

12 Claims, 6 Drawing Sheets

(51) Int. Cl.
*B01J 14/00* (2006.01)
*B01J 20/22* (2006.01)
*B01J 20/26* (2006.01)
*B01J 47/024* (2017.01)
*C07D 213/36* (2006.01)
*C07D 295/027* (2006.01)

(52) U.S. Cl.
CPC ............ *B01J 20/26* (2013.01); *B01J 47/024* (2013.01); *C07D 213/36* (2013.01); *C07D 295/027* (2013.01); *B01J 2219/00191* (2013.01)

(58) Field of Classification Search
USPC .................................. 422/603, 129, 554, 504
See application file for complete search history.

(56) References Cited

U.S. PATENT DOCUMENTS

| | | |
|---|---|---|
| 2003/0158421 A1 | 8/2003 | Wurziger et al. |
| 2006/0245970 A1 | 11/2006 | Lee |
| 2010/0034700 A1 | 2/2010 | Rousseau et al. |
| 2011/0070160 A1 | 3/2011 | Nutt et al. |
| 2016/0274093 A1 | 9/2016 | Earl et al. |

OTHER PUBLICATIONS

Ley et al., "New Tools and Concepts for Modern Organic Synthesis", Nature Reviews, Drug Discovery, 2002, vol. 1, pp. 573-586.
Luescher et al., "SnAP Reagents for the Synthesis of Piperazines and Morpholines", Organic Letters, 2014, vol. 16, pp. 1236-1239.
Siau et al., "One-Step Synthesis of Saturated Spirocyclic N-Heterocycles with Stannyl Amine Protocol (SnAP) Reagents and Ketones", Journal of the American Chemical Society, 2014, vol. 136, pp. 17726-17729.
ThalesNano., "H-Cube. Next Generation Hydrogenation", Brochure www.thalesnano.com.
Tu et al, "Tandem Click-Suzuki reactions in a novel flow reactor incorporating immobilized and exchangeable reagents", RSC Advances, Royal Society of Chemistry, 2015, vol. 5:7, pp. 4754-4757.
Vo et al., "SnAP Reagents for the Transformation of Aldehydes into Substituted Thiomorpholines—An Alternative to Cross-Coupling with Saturated Heterocycles", Angewandte Chemie, 2013, vol. 52, pp. 705-1708.
Vo et al, "SnAP reagents for the one-step synthesis of medium-ring saturated N-heterocycles from aldehydes", Nature Chemistry, 2014, pp. 310-314.

\* cited by examiner

APPARATUS AND PROCESS FOR THE AUTOMATED CHEMICAL SYNTHESIS OF COMPOUNDS

CROSS-REFERENCE TO RELATED APPLICATIONS

This application is the United States national phase of International Application No. PCT/EP2017/050400 filed Jan. 10, 2017, and claims priority to European Patent Application No. 16150878.3 filed Jan. 12, 2016, the disclosures of which are hereby incorporated in their entirety by reference.

BACKGROUND OF THE INVENTION

Field of the Invention

The present invention relates to an apparatus for the automated chemical synthesis of at least one compound, a process for the automated chemical synthesis of at least one compound and a cartridge.

Description of Related Art

In the last decades chemistry has evolved greatly and new technologies and reactions are discovered faster than ever before. However the key processes in organic chemistry have not changed for decades. Even today, many chemical compounds for basic research are still synthesized using laborious and resources inefficient processes, and in practice, synthetic chemistry still requires highly trained chemists. The process is time consuming since new reactions are setup following the careful weighing of chemicals and the addition of solvents, and after completion of the reaction, a tedious workup and purification has to be conducted.

Slow reacting compounds cause further problems in organic synthesis and excess reagents or harsh conditions are often required to push the reactions to higher conversions within a reasonable time frame, which can cause problems in the purification step. As a result, there is a great demand for automation and simplification of such chemical processes.

SUMMARY OF THE INVENTION

One object of the present invention is thus to address these limitations of organic synthesis by enabling an unskilled user to rapidly synthesize organic compounds, in a fully automated manner that obviates the need to weigh and measure all but one of the reaction components, avoids the use of excess reagents, eliminates tedious reaction workups, and ultimately allows faster reaction times.

Another object is aimed mainly at aiding chemical research and development organizations, as it can greatly simplify the way in which key scaffolds are produced for research.

Yet another object is to provide a fully automated, flow chemistry-based synthesizer, which will utilize disposable polymer-supported reagents cartridges, for the production of key scaffolds, such as saturated N-Heterocycles, which are key building blocks in many pharmaceutical and agricultural products. However, unlike their aromatic counterparts, there are limited strategies for the facile construction of substituted saturated N-Heterocycles by convergent, predictable methods.

Even the recently widely adopted SnAP methodology of choice (Vo et al., Nature Chemistry, 2014, pages 310-314) has its limitations. It requires the user to handle highly toxic reagents and perform tedious workup procedures. In addition, in the original solution-phase approach for the synthesis of saturated N-heterocycles, several steps requiring user intervention are necessary, including imine formation, addition of $Cu(OTf)_2$, workup and purification. Each step is separated by a waiting period, which in total builds up to 12-24 h. If several compounds need to be produced, this multi-step methodology is rendered too time consuming. Therefore there is a great demand for novel, automated methods that enable the synthesis of these compounds and many others, in a simple, rapid and highly efficient manner.

These and other objects were solved by providing an apparatus with features described herein and a process with features described herein.

Accordingly, an apparatus for the automated synthesis of at least one chemical compound, in particular for compounds comprising at least one N-heterocyclic structure, is provided, wherein the apparatus comprises:
  at least one cartridge comprising
    at least one first compartment for providing at least one first reagent for the chemical synthesis of the at least one compound;
    at least one second compartment for providing at least one second reagent for the chemical synthesis of the at least one compound, and
    at least one third compartment for purifying the at least one synthesized compound.
  at least one reaction container for providing the compounds to be fed into at least one of the compartments of the cartridge and/or collecting the reaction product from at least one of the compartments of the cartridge;
  at least one solvent container for storing the solvent systems used for at least one of the compartments of the cartridge;
  optionally at least one waste container for collecting the waste from at least one of the compartments of the cartridge, in particular one waste container for all of the at least three compartments;
  at least two flow path selecting valves, wherein at least one first valve selects the liquid source, in particular reaction container or solvent reservoir, and the at least one second valve directs the liquid to one of the compartments in the cartridge, reaction container or optional waste container, and
  at least one pump arranged downstream of the at least one first valve and upstream of the at least one second valve, i.e. the pump transfers or pumps the selected liquid from the at least one first valve to the at least one second valve.

Thus, an apparatus is provided that comprises separate vessels for storage of the solvents and optional waste, and at least one separate container for either the delivery of the substrate, storage of the intermediate products, or the final products. The present apparatus enables a passing of the substrate, intermediate product and/or reaction product from the vessels or container through the different compartments of the cartridge. The solution phase can be recycled multiple times through each of the compartments comprising the physically separated reagents to give improved reaction yields. In addition the flow through each of the compartments of the cartridge can be independently controlled. That allows recycling through a specific compartment of the cartridge and thus contact with the respective reagent for as long as required. This offers a significant advantage over a single pass through each compartment since the flow rate through each compartment and number of cycle times can be controlled to optimize the yield, and enables chemical reactions that would not be possible using a single pass method.

The cartridge that is provided in the present apparatus is separated into several compartments, wherein the cartridge comprises at least one compartment for each of the three steps: first reagent compartment, second reagent compartment and purification compartment. In the present cartridge all essential components required for the chemical synthesis are contained in the compartments of the cartridge and which allows a fully automated synthesis.

It is possible to provide the substrate neat or in a different concentration (such as 0.1-1.0 mmol) which reacts with the reagent in the reagent compartment by forming a substrate-reagent intermediate product, which is released from the solid support of the at least one first reagent compartment. Furthermore, a range of alternative immobilized reagents can be used enabling the synthesis of a broad range of different compounds. Further, the first reaction product can be passed through the second reagent compartment (which comprises for example a non-immobilized reactant in catalytic or stoichiometric amounts) to trigger a transformation.

In an embodiment the cartridge comprises at least one further fourth compartment for removing any (non-reacted) reagent material, such as any catalyst material, from the reaction mixture.

It is in general to be understood that the there is no specific arrangement order of the compartments. The order rather depends on the specific chemical reaction requirements. Thus, in one embodiment the order may be first reagent compartment, second reagent compartment, purification compartment. In another embodiment the order may be first reagent compartment, purification compartment, and second reagent compartment. There also may be more than one purification compartment. In this case the order may be first reagent compartment, first purification compartment, second reagent compartment, and second purification compartment. Any combination of the compartments is possible.

The compartments of the cartridge may preferably have a cylindrical shape with different lengths for example a length in a range between 50 and 150 mm, preferably between 70 and 100 mm, and a diameter between 5 and 15 mm, preferably between 8 and 10 mm. The cartridge and compartments may be made of plastic material, respectively. Furthermore, cartridge and compartments may be made in one piece.

The compartments may be spatially separated from each other and/or arranged next to each other, for example parallel or in line.

It also preferred that each of the compartments comprises at least one inlet and one outlet. Thus, each compartment is connected via inlet and outlet to a reaction container and/or a solvent reservoir.

Thus, the cartridge with the three or four compartments is coupled to at least one reaction container storing the starting material and/or the reaction products of each compartment and at least one solvent reservoir for storing the solvent required for the different reaction sequences in the compartments of the cartridge and optionally at least one waste container.

It is however also conceivable that at least one reaction container and/or at least one solvent reservoir is assigned to each single one of the compartments. The number of reaction containers and/or solvent reservoirs can thus vary and depend on the specific process requirements.

In a preferred embodiment of the present apparatus each of the compartments of the cartridge comprises
  at least one inlet that is operatively linked to the at least one second valve that directs the liquid to one of the compartments in the cartridge, and
  at least one outlet that is operatively linked to the at least one reaction container and optionally at least one waste container.

In an embodiment of the present apparatus the at least one cartridge comprises
  at least one first compartment A comprising the first reagent as at least one immobilized reagent;
  at least one second compartment B comprising at least one catalyst as the second reagent;
  at least one third compartment C comprising at least one scavenging matrix for removing the at least one catalyst from the reaction mixture, and
  at least one fourth compartment D comprising at least one ion exchange support for purifying the reaction product,

It is furthermore preferred, if the at least one third compartment C of the at least one cartridge comprises at least one scavenging matrix for removing the at least one catalyst selected from a group comprising polymer-supported thiourea, polymer-supported trisamine and silica-supported trisamine.

It also preferred, if the at least one fourth compartment D of the at least one cartridge comprises an ion exchange resin or a silica supported ion exchange such as solid supported sulfonic acid, for purifying the reaction product.

In a preferred embodiment the cartridge used in the present apparatus for the chemical synthesis of at least one compound comprising at least one N-heterocyclic structure, wherein said cartridge comprises the following compartments at least one of the followings:
  at least one first compartment A
    comprising the first reagent as at least one of an immobilized Sn-containing reagent (SnAP reagent) of the general formulae (Ia)

or of the general formulae (Ib)

wherein
  $R^1$, $R^2$, $R^3$, $R^{10}$ are selected from a group comprising alkyl, wherein $R^1$, $R^2$, $R^3$ can be the same or different;
  X is selected from a group comprising O, protected N, S;
  $R^4$, $R^5$, $R^6$, $R^7$ are selected from a group comprising H, alkyl, cycloalkyl, alkenyl, cycloalkenyl, aryl, wherein $R^4$, $R^5$, $R^6$, $R^7$ can be the same or different; and/or
  at least one of $R^4$, $R^5$ and at least one of $R^6$, $R^7$ together form an alkyl or aryl ring system, or
  at least two of $R^4$ and $R^5$ or at least two of $R^6$, $R^7$ together form a alkyl or aryl spirocyclic ring system, which can be interrupted by one or multiple oxygen atoms, sulphur atoms, substituted and/or unsubstituted nitrogen atoms and/or by one or multiple groups of the type —C(O)O—, —OC(O)—, —C(O)—, —NHC(O)O—, —OC(O)NH— and/or —OC(O)O,
  n, m=1-6, preferably 1-5, 1, 2, 3, 4, 5, $Y=P(R^{11})_2$, wherein $R^{11}$ can be at least one alkyl or aryl, carrier is a polymer or a silica compound, such as a silica gel, wherein the at least of Sn-containing reagent of general formulae (Ia) or (Ib) is able to react with at least one aldehyde of the general formulae (IIa)

$R^8$—CHO or at least one ketone of the general formulae (IIb)

$R^8R^9CO$ wherein $R^8$ and $R^9$ are selected from a group comprising alkyl, alkenyl, cycloalkyl, cycloalkenyl, —COOR$^{12}$ (R$^{12}$ being alkyl), aryl, heteroaryl, which are in each case non-substituted or substituted; or where $R^8$ and $R^9$ are joined to form an alkyl or aryl ring system, in particular a $C_4$-$C_8$ alkyl ring, which can be interrupted by one or multiple oxygen atoms, sulphur atoms, substituted and/or unsubstituted nitrogen atoms and/or by one or multiple groups of the type —C(O)O—, —OC(O)—, —C(O)—, —NHC(O)O—, —OC(O)NH— and/or —OC(O)O, to form at least one imine or ketimine;

at least one second compartment B comprising the second reagent as at least one catalyst for cyclization of the at least one imine or the at least one ketimine leaving the first compartment A to at least one N-heterocyclic compound of the general structure (IIIa)

or of the general structure (IIIb)

or of the general structure (IIIc)

wherein $R^4$-$R^9$ have the above meanings wherein the at least one cyclization catalyst is selected from a group comprising a transition metal salt, such as a copper salt or a Scandium salt, at least one third compartment C comprising at least one scavenging matrix for removing the at least one cyclization catalyst from the reaction mixture comprising the N-heterocyclic compound leaving the at least one second compartment B, at least one fourth compartment D comprising at least one ion exchange support for purifying the N-heterocyclic reaction product.

Thus, the cartridge provides all essential components required for the synthesis of N-heterocycles. The immobilized reagents in the compartments of the cassette or cartridge allow a fully automated synthesis. Furthermore, a range of alternative immobilized reagents can be used. In particular, many different immobilized SnAP reagents can be used to fill the preferably disposable cassettes or cartridges, enabling generation of a broad range of different saturated N-heterocycles.

In an embodiment of the present cartridge the at least one first compartment A comprises at least one of a polymer immobilized Sn-containing reagent of the general formulae (Ia)

or of the general formulae (Ib)

wherein $R^1$, $R^2$, $R^3$, $R^{10}$ are selected from a group comprising $C_1$-$C_{10}$ alkyl, preferably $C_1$-$C_6$ alkyl, in particular preferably $C_4$ alkyl such as butyl, tert-butyl, isobutyl, wherein $R^1$, $R^2$, $R^3$ can be the same or different;

X is selected from a group comprising O, protected N, S;

$R^4$, $R^5$, $R^6$, $R^7$ are selected from a group comprising H, $C_1$-$C_{20}$ alkyl, $C_5$-$C_{10}$ cycloalkyl, $C_2$-$C_{20}$ alkenyl, $C_5$-$C_{10}$ cycloalkenyl, $C_6$-$C_{12}$ aryl, wherein $R^4$, $R^5$, $R^6$, $R^7$ can be the same or different; and/or at least one of $R^4$, $R^5$ and at least one of $R^6$, $R^7$ together form a 5 to 12 membered alkyl or aryl ring system, in particular a 6 membered alkyl or aryl ring system, such as C6 aryl ring, or at least two of $R^4$ and $R^5$ or at least two of $R^6$, $R^7$ together form a 4-7 membered alkyl or (hetero-)aryl sprirocyclic ring systems;

which can be interrupted by one or multiple oxygen atoms, sulphur atoms, substituted and/or unsubstituted nitrogen atoms and/or by one or multiple groups of the type —C(O)O—, —OC(O)—, —C(O)—, —NHC(O)O—, —OC(O)NH— and/or —OC(O)O, n, m=1, 2, 3, 4, 5, $Y=P(R^{11})_2$, wherein $R^{11}$ is aryl, in particular Ph;

carrier is polystyrene, wherein the at least of Sn-containing reagent of general formulae (Ia) or (Ib) is able to react with at least one aldehyde of the general formulae (IIa)

$R^8$—CHO or at least one ketone of the general formulae (IIb)

$R^8R^9CO$ wherein $R^8$ and $R^9$ are selected from a group comprising $C_1$-$C_{20}$ alkyl, $C_2$-$C_{20}$ alkenyl, $C_5$-$C_{10}$ cycloalkyl, $C_5$-$C_{10}$ cycloalkenyl, —COOR$^{12}$ (R$^{12}$ being $C_1$-$C_{10}$ alkyl), $C_6$-$C_{12}$ aryl, or where $R^8$ and $R^9$ are joined to form an $C_5$-$C_{12}$ alkyl or $C_6$-$C_{12}$ aryl ring system, in particular a C6 aryl ring which can be interrupted by one or multiple oxygen atoms, sulphur atoms, substituted and/or unsubstituted nitrogen atoms and/or by one or multiple groups of the type —C(O)O—, —OC(O)—, —C(O)—, —NHC(O)O—, —OC(O)NH— and/or —OC(O)O, to form at least one imine or ketimine.

The moieties $R^4$, $R^5$, $R^6$, $R^7$ can be selected from a group comprising H, $C_1$-$C_{12}$ alkyl, $C_5$-$C_7$ cycloalkyl, $C_2$-$C_{12}$ alkenyl, $C_6$-$C_{12}$ aryl or heteroaryl, in particular methyl, ethyl, propyl, phenyl (unsubstituted or substituted with F, Cl, CF$_3$), pyridine.

Preferred Examples for Sn-containing reagent of general formulae (Ia) or (Ib) are

-continued

In a more specific embodiment the following Sn-containing reagents are provided:

-continued

In another variant of the present cartridge the at least one second compartment B comprises at least one catalyst selected from a group comprising Cu and Sc salts (such as $ScCl_3$), in particular $Cu(Z)_2$ wherein Z is selected from a group containing OTf, Cl, Br, $SO_4^{2-}$, in particular $Cu(OTf)_2$.

In yet another variant of the present cartridge the at least one third compartment C comprises at least one scavenging matrix for removing the at least one cyclization catalyst selected from a group comprising polymer-supported thiourea, polymer-supported trisamine and silica-supported trisamine.

In still another variant of the present cartridge the at least one fourth compartment D comprises an ion exchange resin or a silica supported ion exchange such as solid supported sulfonic acid, for purifying the N-heterocyclic reaction product.

The cartridge of the present apparatus is preferably placed in a cartridge holder that may be coupled to the synthesis apparatus.

The cartridge holder may comprise two parts wherein at least one part of the cartridge holder is heated and the other part of the cartridge holder is not heated. The heated section of the cartridge holder comprises also at least one heating unit and is made of a suitable metal, such as aluminum. The non-heated section of the cartridge holder is kept at room temperature and is preferably made of plastics such as polypropylene/polycarbonate. Such asymmetrical arrangement of heated and non-heated section (which may be also color coded) may also prevent an erroneous insertion of the cartridge into the cartridge holder. This is important since in one embodiment only the three compartments A-C should be heated whereas the fourth compartment D should be kept at room temperature.

Accordingly, in an embodiment the heated section of the cartridge holder is adapted to house any of the compartments comprising the first reagent and the second reagent, such as a catalyst, and the non-heated section of the cartridge holder is adapted to house the purification compartment. In a specific embodiment the cartridge holder is adapted to house the compartments A, B and C and the non-heated section of the cartridge holder is adapted to house the compartment D.

As stated above, the present apparatus is coupled to at least one reaction container for providing the compounds to be fed into at least one of the compartments of the cartridge, in particular into at least one of the compartments A-D of the cartridge and/or collecting the reaction product from at least one of the compartments, in particular of the compartments A-D of the cartridge; in particular one reaction container for all of the at least four compartments. Thus, the reaction container(s) used in the present apparatus and the below described process can be the same or different. For example one reaction container is used repeatedly for all educts and products. It is also possible that one reaction container is used for educts/products from each compartment.

The reaction container may provide the starting material such as aldehyde/ketone and receive the product. It also acts as reaction container where the reaction liquid is contained. Since the volume of the flow path is smaller than the volume of the solvent used in the reaction the container acts much like a buffer or temporary storage.

The reaction container can be defined as any vessel capable of containing or storing the reactants, intermediates or products from the compartments, for example, as vial, a tubing loop, or a chip-based reactor. The reaction container is also capable of being heated or irradiated with light.

As stated above. the present apparatus is also coupled to at least one solvent reservoir for storing the solvent systems used for at least one of the compartments of the cartridge; in particular solvent reservoirs for all of the at least four compartments A-D. Several solvent reservoirs may be used for the whole apparatus that are not designated to one specific compartment but are used for all compartments of the apparatus.

The present apparatus may further be coupled to at least one waste container for collecting the waste from at least one of the compartments of the cartridge, in particular one waste container for all of the at least three or four compartments. It is however also conceivable to provide one separate waste container for each of the at least three or four compartments.

As also stated above, the present apparatus comprises at least two flow path selecting valves, wherein at least one first valve selects the liquid source, in particular reaction container or solvent reservoir, and the other second valve directs the liquid to one of the compartments, reaction container or waste container. The valves are commercially available components consisting for example of a flow path selecting Teflon valve with attached stepper motors.

The present apparatus comprises also at least one pump for all liquids used in the synthesis process, wherein the at least one pump is arranged downstream of the at least one first valve and upstream of the other second valve. Thus, the at least one pump connects the at least two flow path selecting valves. A commercially available solenoid pump may be used as a pump.

The present apparatus also may comprise at least one stirring unit. Specifically, each reaction container may comprise at least one stirring means. The stirring means may for example consists of four small inductive coils. These are magnetized in a circular fashion to propel a small magnetic stir bar in the reaction container.

In yet another variant the present apparatus comprises at least one microcontroller for operating/controlling the at least two flow path selecting valves, the at least one pump, the at least one heating unit and the at least one stirring unit.

In one further embodiment the apparatus comprises at least one touchscreen. The touchscreen offers a simple, intuitive user interface and sends all commands to the microcontroller to be processed. The apparatus could also be controlled by external interface via RS-232, RS-485 or USB.

It is also possible that the apparatus may also contain further electrical components like a RFID reader for automatic recognition of the inserted cartridges/cartridges and connected compartments.

The present apparatus is used for a process for the automated synthesis of chemical compounds comprising the steps
  providing at least one substrate in at least one solvent in the at least one reaction container;
  automatically passing the at least one substrate through the at least one first reagent compartment once or several times and collecting the formed substrate-reagent intermediate product (i.e. formed when passing the at least one first reagent compartment) in the at least one reaction container prior to passing the substrate-reagent intermediate product into the subsequent compartments;
  automatically passing the substrate-reagent intermediate product through the at least one second reagent compartment once or several times and collecting the formed reaction product (i.e. formed when passing the at least one second reagent compartment) in the at least one reaction container prior to passing the reaction product into the subsequent compartments;
  automatically passing the reaction product through the at least one third compartment for purifying the product once or several times and collecting the purified product in the at least one reaction container.

It is to be understood that the order of the process step may vary. For example, it is possible that the substrate-reagent intermediate leaving the first compartment comprising the first reagent is passed through the purification compartment and only subsequently through the compartment comprising the second reagent followed by another purification step. Any combination is possible and is chosen according to the specific reaction requirements.

In an embodiment of the present process for the automated synthesis of a chemical compound the process comprises the steps:
  providing at least one substrate in at least one solvent in the at least one reaction container;
  automatically passing the at least one substrate once or several times through at least one first compartment A comprising the first reagent as at least one immobilized reagent and collecting the formed substrate-reagent intermediate product in the at least one reaction container prior to passing the substrate-reagent intermediate product into a subsequent compartment B;
  automatically passing the substrate-reagent intermediate product through at least one second compartment B comprising at least one catalyst as the second reagent once or several times and collecting the formed reaction product in the at least one reaction container prior to passing the reaction product into a subsequent compartment C;
  automatically passing the reaction product formed in compartment C through at least one third compartment C comprising at least one scavenging matrix for removing the at least one catalyst from the reaction mixture and collecting the formed reaction product in the at least one reaction container prior to passing the reaction product into a subsequent compartment D; and
  automatically passing the reaction product obtained in compartment C through at least one fourth compartment D comprising at least one ion exchange support for purifying the reaction product once or several times and collecting the purified product in the at least one reaction container.

In an embodiment the process for the automated synthesis of compounds comprising at least one N-heterocyclic structure comprises the steps:

providing at least one aldehyde of the general formulae (IIa) $R^8$—CHO or at least one ketone of the general formulae (IIb) $R^8R^9CO$, wherein $R^8$ and $R^9$ have the above meanings, in at least one organic solvent in at least one reaction container;

passing said aldehyde or ketone solution through the at least one compartment A comprising the at least one immobilized Sn-containing reagent of general formulae (Ia) or general formulae (Ib); and collecting the imine or ketimine solution formed when passing through compartment A in at least one reaction container;

passing said imine or ketimine solution through the at least one second compartment B comprising the at least one cyclization catalyst and collecting the at least one N-heterocyclic compound of the general formulae (IIIa), (IIIb) or (IIIc) formed when passing through compartment B in at least one reaction container;

passing said N-heterocyclic compound of the general formulae (IIIa), (IIIb) or (IIIc) through the at least one third compartment C comprising the at least one cyclization catalyst scavenging matrix and collecting the cyclized catalyst free N-heterocyclic compound of the general formulae (IIIa), (IIIb) or (IIIc) in at least one reaction container;

loading the at least one fourth compartment D comprising at least one ion exchange support with the cyclized catalyst free N-heterocyclic compound of the general formulae (IIIa), (IIIb) or (IIIc), washing the loaded ion exchange support with an appropriate solvent system; eluting the N-heterocyclic reaction product from the ion exchange support using an appropriate solvent system and collecting the eluted N-heterocyclic reaction product in at least one reaction container.

The solutions are passed through compartments A-C by pumping in circular flow for 5 to 120 min, preferably for 10 to 45 min, most preferably for 20 to 30 min at a temperature between 40 and 100° C., preferably between 50 and 80° C., most preferably between 60 and 70° C. In general the applied temperature of the heating unit should not raise more than 20° C. above the boiling point of the solvent used in the reaction.

In case of compartment D the solutions are passed through by pumping in circular flow for 5 to 60 min, preferably for 10 to 45 min, most preferably for 20 to 30 min at room temperature.

Within the meaning of the present invention circular flow means that liquid is pumped from reaction container to flow path selecting valve A to pump to flow path selecting valve B through one of the compartments of the cartridge into the reaction container.

The maximum flow rate for the used pump is given to be 24 ml/min for water from the manufacturer. In case of the used solvents a maximum flow rate of 10 ml/min is possible. The flow rate is adjusted such that no back pressure is experienced.

The different reaction steps in compartments A-D may require specific solvents. For example, the imine/ketimine formation in compartment A is carried out in $CH_2Cl_2$. The cyclization in Compartment B uses in particular acetonitrile, 2,6-lutidine, $CH_2Cl_2$ or HFIP as organic solvent. The scavenging step in compartment C uses preferably $CH_2Cl_2$, $C_2H_4Cl_2$, or MeOH.

In compartment D the loaded support is preferably washed with an organic solvent such $CH_2Cl_2$ and MeOH; wherein the N-heterocyclic reaction product is eluted from the resin using preferably a mixture of an amine in MeOH or 0.1M $NH_3$ in MeOH.

In general the type of solvent or solvent mixture is determined by the educts and products and can thus vary.

In a variant of the present process the reaction product is eluted from the at least one purifying compartment after the cartridge is removed by the user from the apparatus. In particular the at least one fourth compartment D with loaded N-heterocyclic reaction product is removed by the user from the apparatus and the N-heterocyclic product is eluted separately at any time using the appropriate solvent system.

BRIEF DESCRIPTION OF THE DRAWINGS

The invention is described in more detail by means of the following examples with reference to the Figures. It shows.

DESCRIPTION OF THE INVENTION

Figure 1:
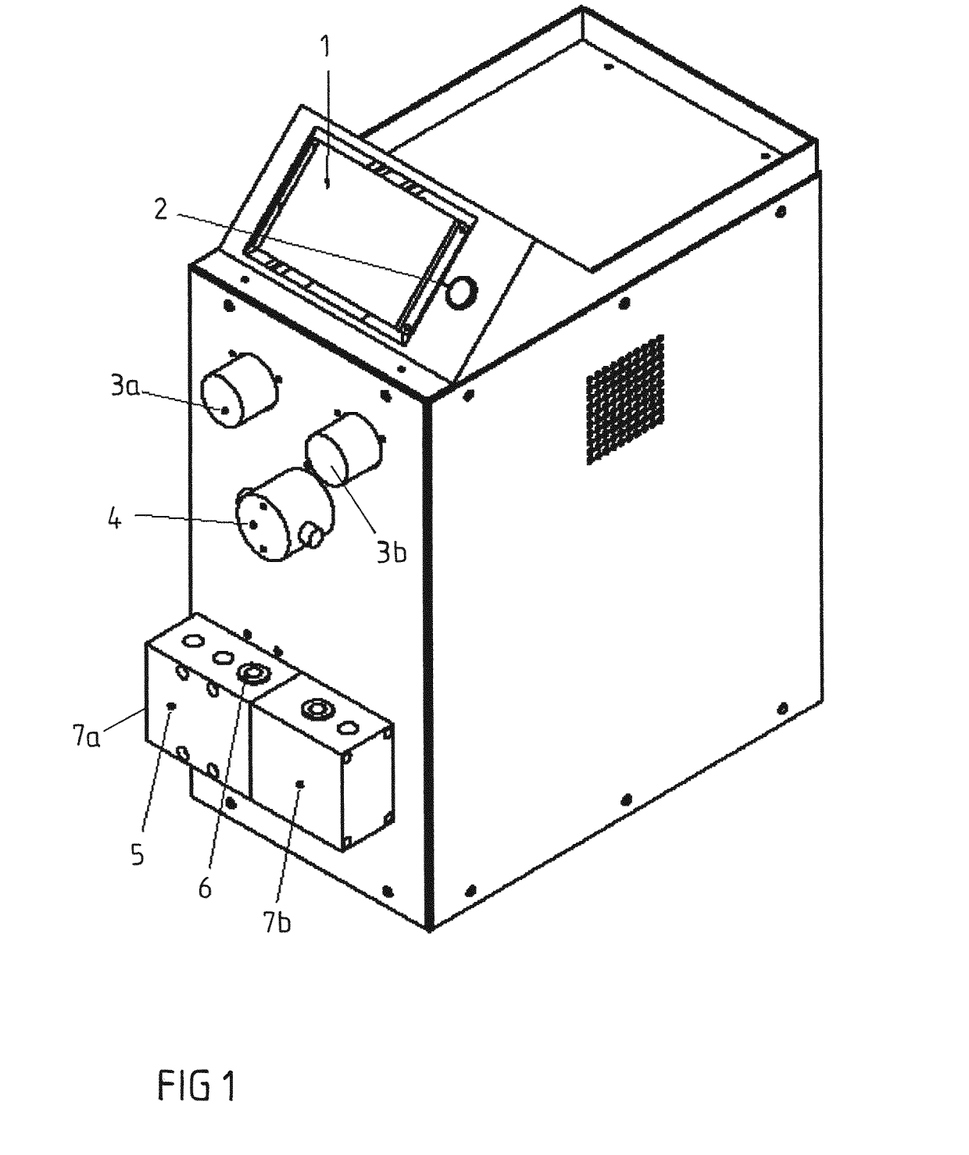
FIG. 1 an embodiment of an apparatus according to an embodiment of the present invention.

In FIG. 1 an embodiment of the automatic synthesizer or apparatus is depicted. The apparatus comprises a Touch-screen 1, On/Off Button 2, two Flow path selecting valves 3a,b, a Pump 4, a heating unit 5 preferably made of Aluminum, a single cartridge 6 inserted in the section of a heated cartridge holder 7a, the non-heated section of the cartridge holder 7b.

Figure 2A:
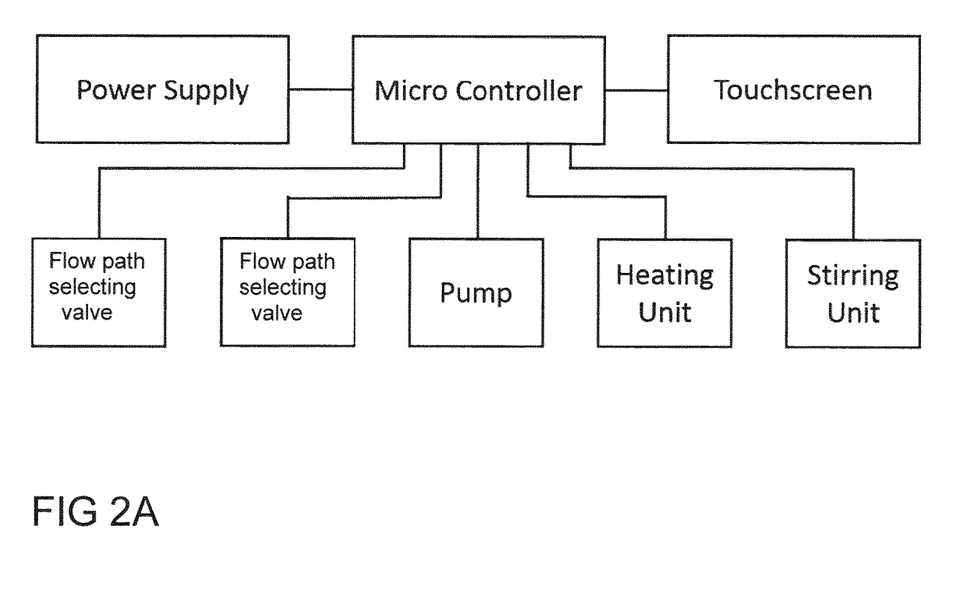
FIG. 2A a scheme of electrical components of an apparatus for automated synthesis according to an embodiment of the present invention.

FIG. 2A shows a general scheme of the different electrical components required in the present apparatus for automated synthesis of N-heterocyclic structures.

A common 12V power supply feeds power to the central microcontroller board. It handles the whole program and directs the necessary power to the individual components. The touchscreen offers a simple, intuitive user interface and sends all commands to the microcontroller to be processed. The apparatus could also be controlled by an external interface via RS-232, RS-485 or USB. From the user commands obtained, the microcontroller operates the two flow path selecting valves, pump, heating unit and a stirring unit. The valves are commercial available components consisting of a flow path selecting Teflon valve with attached stepper motors. A commercial available pump is used here, for example a solenoid pump. The heating unit is composed of aluminum with four heating capsules inside. A temperature probe measures the current temperature and the microcontroller adjusts the heating power to the temperature set by the user. The stirring unit consists of four small inductive coils.

These are magnetized in a circular fashion to propel a small magnetic stir bar in the reaction container. The machine may also contain further electrical components like a RFID reader for automatic recognition of the inserted cartridge.

Figure 2B:
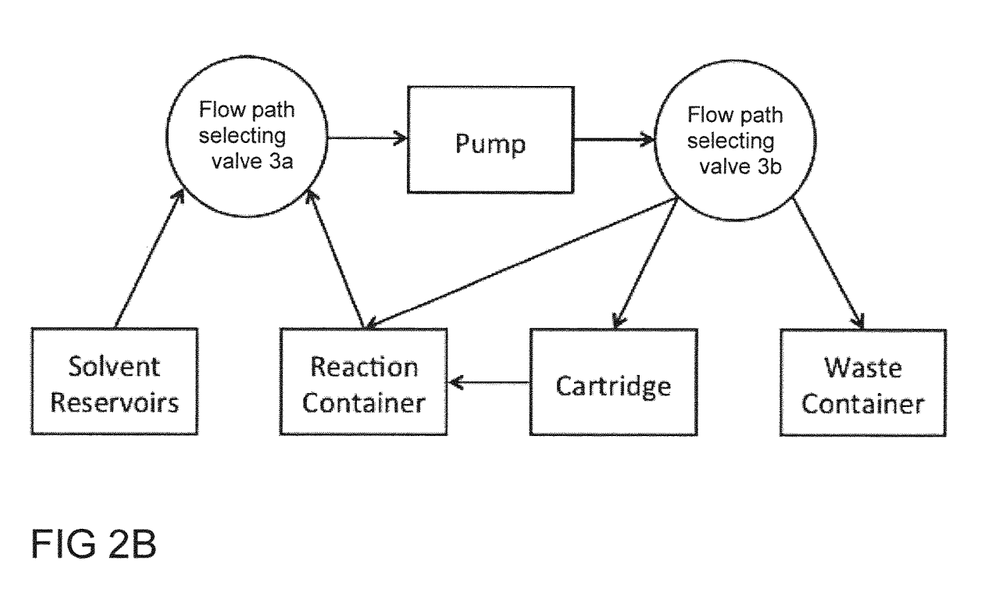
FIG. 2B a general flow scheme for liquids in an apparatus according to one embodiment of the present invention.

The scheme depict in FIG. 2B provides an overview of a general flow scheme for liquids in the automated synthesizer. The automated synthesizer uses two 8-port flow path selecting valves and a pump to handle all liquids during the process. One valve has the task of selecting the source of liquid for the pump (solvent reservoirs/reaction container). The other valve chooses the destination of the liquid or reagent (Waste Container/Reagent Compartments/Reaction Container).

The scheme depict in FIG. 2B provides an overview of a general flow scheme for liquids in the automated synthesizer. The automated synthesizer uses two 8-port flow patch selecting valves and a pump to handle all liquids during the process. One valve has the task of selecting the source of liquid for the pump (solvent reservoirs/reaction container). The other valve chooses the destination of the liquid or reagent (Waste Container/Reagent Compartments/Reaction Container).

Figure 3:
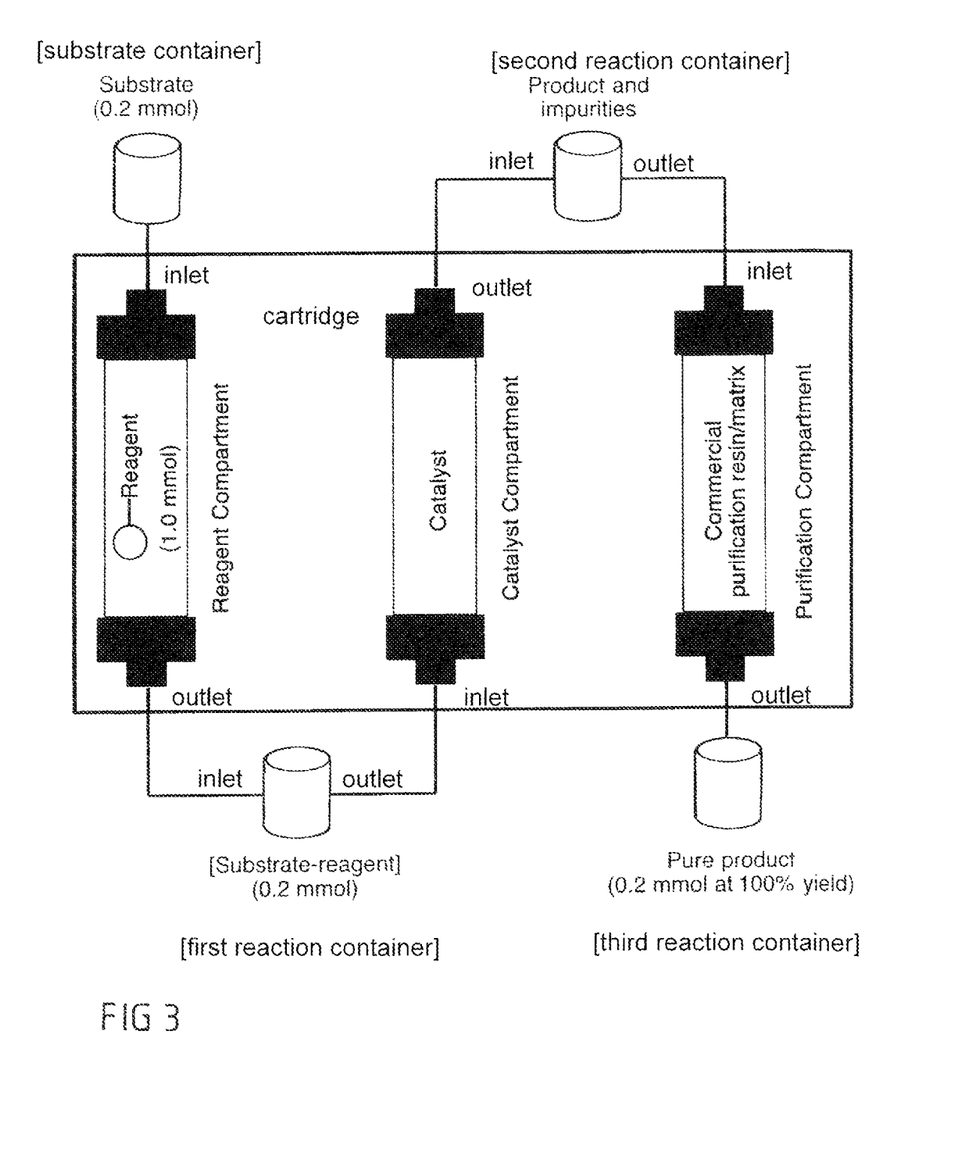
FIG. 3 an embodiment of a cartridge according to the invention.
Figure 3A:
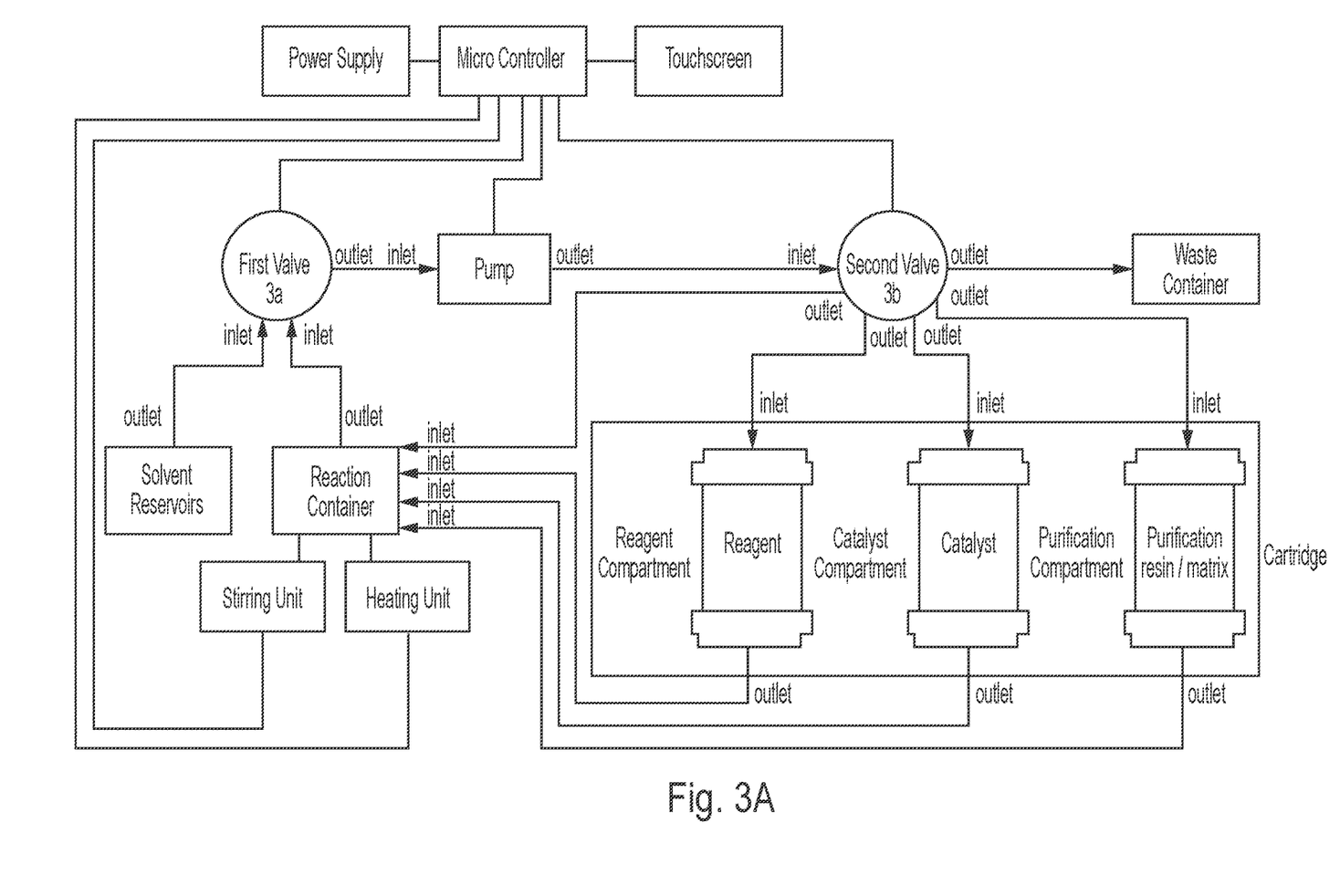
FIG. 3A a scheme of components of an apparatus according to an embodiment of the present invention.

The basic concept of the present invention is explained by means of the embodiment of a cartridge shown in FIG. 3. In the basic concept there is one cartridge which is separated into several, at least three compartments. The cartridge contains at least one compartment for each of the three steps (Reagent compartment, second reagent compartment, Purification compartment).

The substrate can be delivered neat or a substrate concentration range of between 0.1 and 1.0 mmol can be used. The machine is capable of dissolving the substrate given to adjust it to the required concentration. The substrate reacts with the reagent in the reagent compartment and the resulting reagent is released from the solid support. Therefore only the desired amount of reagent is released avoiding any contamination with excess reagent. According to the example in FIG. 3 0.2 mmol substrate reacts in the reagent compartment containing 1.0 mmol reagent on a polymer support. Only 0.2 mmol is then released as [substrate-reagent] intermediate product. 0.8 mmol reagent remains on polymer support in the reagent compartment.

The substrate-reagent intermediate product is then fed into a second reagent (a catalyst or stoichiometric reagent) compartment and the desired product is formed and collected in a reaction container. The product containing impurities is then fed into the purification compartment containing a commercial purification resin/matrix and the purified product is collected.

Figure 4:
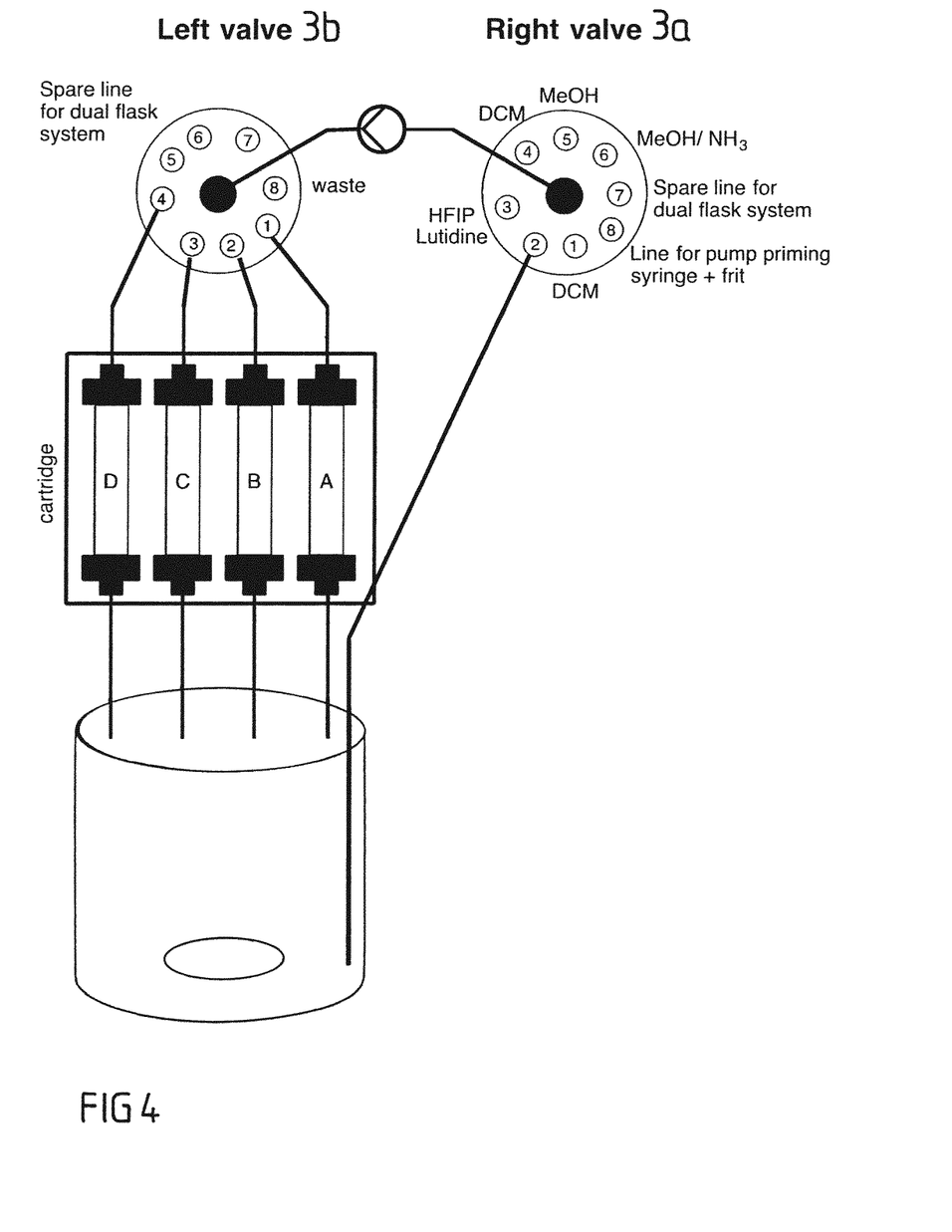
FIG. 4 a further flow scheme for liquids in an apparatus and a cartridge according to another embodiment of the present invention.

The flow scheme of FIG. 4 shows an embodiment of the invention. Here the cartridge comprises four compartments A-D. The inlets of each of the compartments are coupled to one flow path selecting valve (left valve 3b). Said left valve 3b selects the flow of the liquid or substrate into one of the four compartments. Outlet 1 of the left valve 3b is coupled to compartment A, outlet 2 is coupled to the inlet of compartment B, outlet 3 is coupled to the inlet of compartment C and outlet 4 is coupled to the inlet of compartment D. The outlets of each of the compartments A-D are connected to a reaction container which contains a stirring element. The other valve (right valve 3a) selects the source of liquid for the pump (solvent reservoirs/reaction container).

Figure 5:
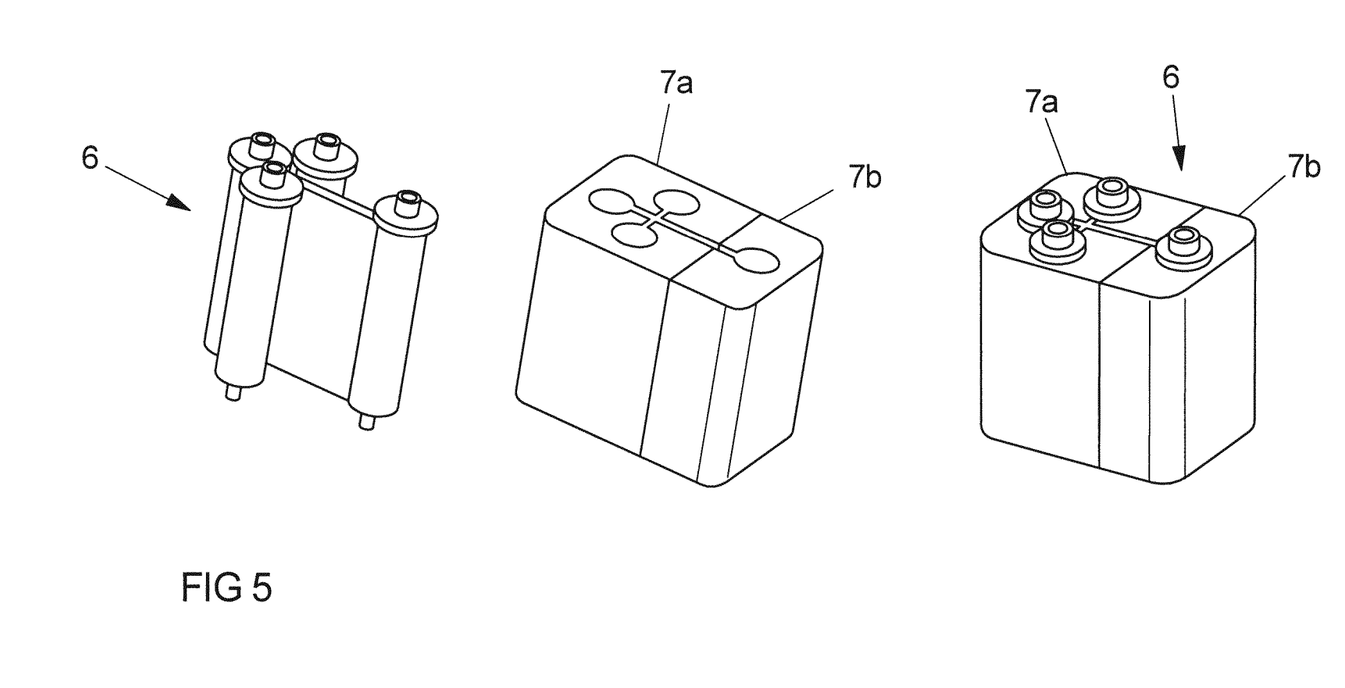
FIG. 5 an embodiment of a cartridge holder.

The cartridge holder shown in FIG. 5 comprises two sections: a heated metal section 7a and a non-heated section 7b made of polypropylene. The cartridge 6 comprising the four compartments A-D is inserted into the holder such that compartments A-C are placed in the heated section 7a and compartment D is placed in the non-heated section 7b.

Example Procedure:

a) Step A: Imine/Ketimine Formation

To start the process a user has to insert a new cartridge into the cartridge holder and provide the aldehyde or ketone (0.1 to 0.5 mmol) in the defined reaction container containing a small magnetic stir bar into the holder in the machine. The synthesizer adds solvent (4 mL DCM or DCE) to the starting material from the solvent reservoir by flowing it through compartment A of the cartridge containing 1.5 mmol of the immobilized SnAP reagent.

Step A: Imine Formation

Afterwards the solution is pumped through compartment A via circular flow for 15 min at 60° C. to form the imine. The residual reagent in compartment A is then washed out with 4 mL DCM or DCE from the solvent reservoir to the reaction container.

b) Step B: Cyclization

To this solution 2 mL HFIP and 2,6-lutidine (0.5 mmol) are added from the solvent reservoirs through compartment B of the cartridge, containing 200 mg $Cu(OTf)_2$, into the reaction container. The mixture is then pumped through compartment B via circular flow for 30 min at 60° C. while stirring the reaction container. The residual reagent in compartment B is then washed out with 4 mL DCM or DCE from the solvent reservoir to the reaction container.

Step B: Cyclization

Examples of cyclization products include c) Step C: Scavenging

The product containing solution in the reaction container is then pumped through the compartment C containing 500 mg Cu scavenging resin for 10 min at 60° C. via circular flow to remove copper compounds in the mixture. The residual reagent in compartment C is then washed out with 4 mL DCM or DCE from the solvent reservoir to the reaction container.

Step C: Copper scavenging d) Step D: Product Purification

For purification of the product the mixture is pumped through the product catch compartment D, containing 1 g of ion exchange resin, for 10 min at room temperature to catch all product on the resin. The solid support is then washed with 10 mL of MeOH from the solvent reservoir to wash out all impurities.

The waste solution in the reaction container is then pumped into the waste and the container itself is washed with DCM and MeOH from the solvent reservoir which is then pumped into the waste as well.

In the last step the product on the resin is eluted from compartment D using a solution of $NH_3$ in MeOH (5 mL, 0.1M) from the solvent reservoirs into the reaction container.

Alternatively the product containing cartridge can be removed by the user and compartment D purged with $NH_3$ in MeOH to release the product manually.

Step D: Amine purification by ion exchange

The following table summarizes the process step-by-step. The SnAP process is run in a single flask system using 0.5 mmol aldehyde as a substrate. The numbers for valve A and B refer to the port number that the rotary valve is set to. The pump speed value refers to an arbitrary set value (1-20), which reflects speed values between 0% and 100% of the maximum speed.

The concentration refers to the concentration of the aldehyde or its conversion products. The concentration decreases over time since a small volume of solvent is added in some steps to wash the compartments.

| valve B | valve A | pump speed | Add solvent | time | magnetic stirrer | heater | Remarks | Conc. (M) |
|---|---|---|---|---|---|---|---|---|
| 1 | 1 | 8 | 4 mL | | off | 60° C. | add solvent/dissolve aldehyde | 0.125 |
| 1 | 2 | 10 | — | 10 min | off | 60° C. | imine or ketimine formation | 0.125 |
| 1 | 1 | 8 | 4 mL | | off | 60° C. | wash compartment A | 0.042 |
| 2 | 3 | 8 | 2 mL | | on, speed = 13 | 60° C. | add HFIP and ligand | 0.036 |
| 2 | 2 | 10 | — | 30 min | on, speed = 13 | 60° C. | cyclization by flow through compartment B | 0.036 |
| 2 | 4 | 8 | 4 mL | | on, speed = 13 | 60° C. | wash compartment B | 0.023 |
| 3 | 2 | 10 | — | 10 min | off | 60° C. | metal removing in compartment C | 0.023 |
| 3 | 4 | 8 | 4 mL | | off | 60° C. | wash compartment C | 0.019 |
| 4 | 2 | 10 | — | 5 min | off | rt | product catch on solid support in compartment D | 0.019 |
| 4 | 5 | 8 | 10 mL | | off | rt | washing away impurity of compartment D | N/A |

The invention claimed is:

1. An apparatus for the automated synthesis of at least one chemical compound, comprising:
(a) at least one solvent container for storing solvent system(s) used for at least one compartment of at least one cartridge, the at least one solvent container comprising at least one solvent reservoir, the at least one solvent reservoir having an inlet and an outlet,
(b) at least one reaction container for providing compound(s) to be fed into at least one of the compartments of the at least one cartridge and/or collecting reaction product(s) from at least one of the compartments of the at least one cartridge, the at least one reaction container having an inlet and an outlet;

(c) at least one first valve for selecting a liquid source from the at least one solvent reservoir or the at least one reaction container, the at least one first valve having an inlet connected to the outlet of the at least one solvent reservoir and the outlet of the at least one reaction container, and an outlet connected to a pump inlet;

(d) at least one pump comprising a first pump comprising the pump inlet for receiving liquid from the outlet of the first valve and a pump outlet connected to an inlet of at least one second valve for directing the liquid received from the at least one first valve to the at least one second valve either directly or through optional pump(s) of the at least one pump;

(e) the at least one second valve for directing the liquid received from the at least one pump to an inlet of at least one compartment of the at least one cartridge or the inlet of the at least one reaction container, the at least one second valve having the inlet for receiving the liquid from the at least one pump, and an outlet connected to the inlet of the at least one compartment of the at least one cartridge and the inlet of the at least one reaction container; and (f) at least one cartridge comprising:
(i) at least one first compartment for providing at least one first reagent for the chemical synthesis of the at least one compound, the at least one first compartment having the inlet connected to the outlet of the at least one second valve, and an outlet connected to the at least one reaction container for passing a formed substrate-reagent intermediate product into the at least one reaction container;
(ii) at least one second compartment for providing at least one second reagent for the chemical synthesis of the at least one compound, the at least one second compartment having an inlet for receiving the substrate-reagent intermediate product from the outlet of the at least one reaction container, and an outlet connected to the inlet of the at least one reaction container for passing the formed reaction product into the at least one reaction container, and
(iii) at least one third compartment for purifying the at least one synthesized compound, the at least one third compartment having an inlet connected to the outlet of the reaction container for receiving the formed reaction product from the outlet of the first reaction container, and an outlet connected to the inlet of the at least one reaction container for passing the purified product into the at least one reaction container.

2. The apparatus according to claim 1, wherein the at least one cartridge further comprises at least one fourth compartment for removing any (non-reacted) reagent material from the reaction product, the at least one fourth compartment(s) having an inlet connected to the outlet of the at least one reaction container for receiving the purified product from the at least one reaction container and an outlet connected to the inlet of the at least one reaction container for passing purified product into the at least one reaction container.

3. The apparatus according to claim 1, wherein the inlet of each compartment is operatively linked to the at least one second valve that directs the liquid to one of the compartments in the cartridge.

4. The apparatus according to claim 1, wherein the reaction container is any vessel capable of containing or storing the reactants, intermediates or products from the compartments.

5. The apparatus according to claim 1, further comprising at least one stirring unit.

6. The apparatus according to claim 1, further comprising at least one heating unit, at least one stirring unit and at least one microcontroller, the microcontroller being configured for operating or controlling the at least one first valve, the at least one second valve, the at least one pump, the at least one heating unit and the at least one stirring unit.

7. The apparatus according to claim 1, further comprising at least one user interface accessible via touch-screen or push-buttons to start the process.

8. The apparatus according to claim 1, wherein
the at least one first compartment comprises the at least one first reagent as at least one immobilized reagent;
the at least one second compartment comprises at least one catalyst as the at least one second reagent;
the at least one third compartment comprises at least one scavenging matrix for removing the at least one catalyst from the reaction product, and
wherein the apparatus further comprises at least one fourth compartment comprising at least one ion exchange support for purifying the reaction product.

9. The apparatus according to claim 8, wherein the at least one third compartment of the at least one cartridge comprises at least one scavenging matrix for removing the at least one catalyst selected from a group comprising polymer-supported thiourea, polymer-supported trisamine and silica-supported trisamine.

10. The apparatus according to claim 8, wherein the at least one fourth compartment of the at least one cartridge comprises an ion exchange resin or a silica supported ion exchange material for purifying the reaction product.

11. The apparatus according to claim 1, further comprising a first purification compartment comprising an inlet configured for receiving the substrate-reagent intermediate product from the outlet of the at least one reaction container and configured for passing a purified product into the inlet of the at least one reaction container prior to passing the purified product into the at least one second compartment.

12. An apparatus for the automated synthesis of at least one chemical compound, comprising:
(a) at least one solvent container for storing solvent system(s) used for at least one compartment of at least one cartridge, the at least one solvent container comprising at least one solvent reservoir, the at least one solvent reservoir having an inlet and an outlet,
(b) at least one reaction container for providing compound(s) to be fed into at least one of the compartments of the at least one cartridge and/or collecting reaction product(s) from at least one of the compartments of the at least one cartridge, the at least one reaction container having an inlet and an outlet;
(c) at least one first valve for selecting a liquid source from the at least one solvent reservoir or the at least one reaction container, the at least one first valve having an inlet connected to the outlet of the at least one solvent reservoir and the outlet of the at least one reaction container, and an outlet connected to a pump inlet;
(d) at least one pump comprising a first pump comprising the pump inlet for receiving liquid from the outlet of the first valve and a pump outlet connected to an inlet of at least one second valve for directing the liquid received from the at least one first valve to the at least one second valve either directly or through optional pump(s) of the at least one pump;

(e) the at least one second valve for directing the liquid received from the at least one pump to an inlet of at least one compartment of the at least one cartridge or the inlet of the at least one reaction container, the at least one second valve having the inlet for receiving the liquid from the at least one pump, and an outlet connected to the inlet of the at least one compartment of the at least one cartridge and the inlet of the at least one reaction container; and (f) at least one cartridge comprising:
  (i) at least one first compartment for providing at least one first reagent for the chemical synthesis of the at least one compound, the at least one first compartment having the inlet connected to the outlet of the at least one second valve, and an outlet connected to the at least one reaction container for passing a formed substrate-reagent intermediate product into the at least one reaction container;
  (ii) a purification compartment for purifying the substrate-reagent intermediate product, the purification compartment having an inlet for receiving the substrate-reagent intermediate product from an outlet of the at least one reaction container and an outlet configured for passing the purified substrate-reagent intermediate product into the inlet of the at least one reaction container;
  (iii) at least one second compartment for providing at least one second reagent for the chemical synthesis of the at least one compound, the at least one second compartment having an inlet for receiving the substrate-reagent intermediate product from the outlet of the at least one reaction container, and an outlet connected to the inlet of the at least one reaction container for passing the formed reaction product into the at least one reaction container.

* * * * *